(12) United States Patent  
Nardi

(10) Patent No.: US 8,192,380 B2
(45) Date of Patent: Jun. 5, 2012

(54) COMPRESSION DEVICE WITH SOLE

(75) Inventor: Steven Nardi, Taunton, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 1128 days.

(21) Appl. No.: 12/041,816

(22) Filed: Mar. 4, 2008

(65) Prior Publication Data

US 2009/0227917 A1 Sep. 10, 2009

(51) Int. Cl.
*A61H 7/00* (2006.01)
(52) U.S. Cl. ............... 601/151; 601/149; 601/148
(58) Field of Classification Search ........... 128/DIG. 20, 128/882, 892, 893, 894; 602/13; 601/149, 601/152, 151, 148, 150, 27–32, 22, DIG. 17; 36/28, 29, 15, 14, 101; 264/45.7, 46.4, 46.6, 264/244, 310, 311, DIG. 83
See application file for complete search history.

(56) References Cited

U.S. PATENT DOCUMENTS

| 1,629,108 | A | 5/1927 | Lake |
| 1,646,590 | A | 10/1927 | Mildenberg |
| 1,976,656 | A | 10/1934 | Clark |
| 2,037,230 | A | 4/1936 | Hack |
| 2,183,277 | A | 12/1939 | Heilhecker |
| 2,211,057 | A | 8/1940 | Duckoff |
| 2,605,560 | A | 8/1952 | Gouabault |
| 3,631,854 | A | 1/1972 | Fryer |
| 3,786,805 | A | 1/1974 | Tourin |
| 4,013,069 | A | 3/1977 | Hasty |
| 4,029,087 | A | 6/1977 | Dye et al. |
| 4,030,488 | A | 6/1977 | Hasty |
| 4,059,910 | A | 11/1977 | Bryden et al. |
| 4,187,620 | A * | 2/1980 | Selner .............................. 36/28 |
| 4,299,213 | A | 11/1981 | Violet |
| 4,476,638 | A | 10/1984 | Quacquarini et al. |
| 4,696,289 | A | 9/1987 | Gardner et al. |
| 4,721,101 | A | 1/1988 | Gardner et al. |
| 4,779,361 | A | 10/1988 | Kinsaul |
| 4,805,601 | A | 2/1989 | Eischen, Sr. |
| RE32,939 | E | 6/1989 | Gardner et al. |
| RE32,940 | E | 6/1989 | Gardner et al. |
| 4,887,369 | A | 12/1989 | Bailey et al. |
| 4,945,905 | A | 8/1990 | Dye et al. |
| 4,979,953 | A | 12/1990 | Spence |

(Continued)

FOREIGN PATENT DOCUMENTS

EP 1795167 A1 6/2007

(Continued)

OTHER PUBLICATIONS

Extended European Search Report dated May 13, 2009 for related European Application No. 09 154 292.8, 8 pgs.

*Primary Examiner* — Annette Dixon
(74) *Attorney, Agent, or Firm* — Thomas M. Johnston, Esq.

(57) ABSTRACT

A compression device for applying compression to a part of a wearer's body. The device includes a bladder including first and second of fluid impermeable layers secured to one another to define an inflatable chamber. The device includes a substantially rigid counterforce component having an opening. An attachment member extends outward from the first layer of the bladder. The attachment member is received in the opening of the counterforce component to attach the counterforce component to the bladder.

18 Claims, 11 Drawing Sheets

U.S. PATENT DOCUMENTS

| | | | |
|---|---|---|---|
| 5,199,191 A | 4/1993 | Moumdjian | |
| 5,201,758 A | 4/1993 | Glover | |
| 5,321,901 A * | 6/1994 | Kelly | 36/134 |
| 5,345,260 A | 9/1994 | Petralia | |
| 5,354,260 A | 10/1994 | Cook | |
| 5,407,421 A | 4/1995 | Goldsmith | |
| 5,450,858 A | 9/1995 | Zablotsky et al. | |
| 5,462,517 A | 10/1995 | Mann | |
| 5,464,385 A | 11/1995 | Grim | |
| 5,626,556 A | 5/1997 | Tobler et al. | |
| 5,651,196 A | 7/1997 | Hsieh | |
| 5,718,669 A | 2/1998 | Marble | |
| 5,741,295 A | 4/1998 | McEwen | |
| 5,795,312 A | 8/1998 | Dye | |
| 5,848,482 A * | 12/1998 | Bathum | 36/127 |
| 5,931,797 A | 8/1999 | Tumey et al. | |
| 5,954,676 A | 9/1999 | Kramer, III | |
| 5,989,204 A | 11/1999 | Lina | |
| 6,014,823 A | 1/2000 | Lakic | |
| 6,098,313 A | 8/2000 | Skaja | |
| 6,231,532 B1 | 5/2001 | Watson et al. | |
| 6,319,215 B1 | 11/2001 | Manor et al. | |
| 6,358,219 B1 | 3/2002 | Arkans | |
| 6,585,669 B2 | 7/2003 | Manor et al. | |
| 6,592,534 B1 | 7/2003 | Rutt et al. | |
| 6,629,942 B1 | 10/2003 | Tubbs | |
| 6,656,141 B1 | 12/2003 | Reid | |
| 6,665,958 B2 | 12/2003 | Goodwin | |
| 6,685,661 B2 | 2/2004 | Peled | |
| 6,715,218 B2 | 4/2004 | Johnson | |
| 6,736,787 B1 | 5/2004 | McEwen et al. | |
| 6,754,982 B2 | 6/2004 | Reed et al. | |
| 6,865,823 B1 | 3/2005 | Vindriis | |
| 6,945,944 B2 | 9/2005 | Kuiper et al. | |
| 6,990,755 B2 | 1/2006 | Hatfield et al. | |
| 7,100,307 B2 | 9/2006 | Burke et al. | |
| 7,225,491 B2 | 6/2007 | Reed et al. | |
| 7,246,453 B2 | 7/2007 | Kim | |
| 7,452,340 B2 * | 11/2008 | Cook et al. | 601/151 |
| 2001/0018564 A1 | 8/2001 | Manor et al. | |
| 2003/0036771 A1 | 2/2003 | McEwen et al. | |
| 2004/0064976 A1 | 4/2004 | Barteet | |
| 2005/0143682 A1 | 6/2005 | Cook et al. | |
| 2007/0282233 A1 | 12/2007 | Meyer et al. | |
| 2009/0227918 A1 | 9/2009 | Nardi et al. | |
| 2009/0227919 A1 | 9/2009 | Nardi et al. | |
| 2009/0227920 A1 | 9/2009 | Nardi et al. | |
| 2009/0227921 A1 | 9/2009 | Nardi | |
| 2009/0227922 A1 | 9/2009 | Nardi et al. | |

FOREIGN PATENT DOCUMENTS

| | | |
|---|---|---|
| JP | 11-197201 A | 7/1999 |
| WO | 2006065225 A1 | 6/2006 |

* cited by examiner

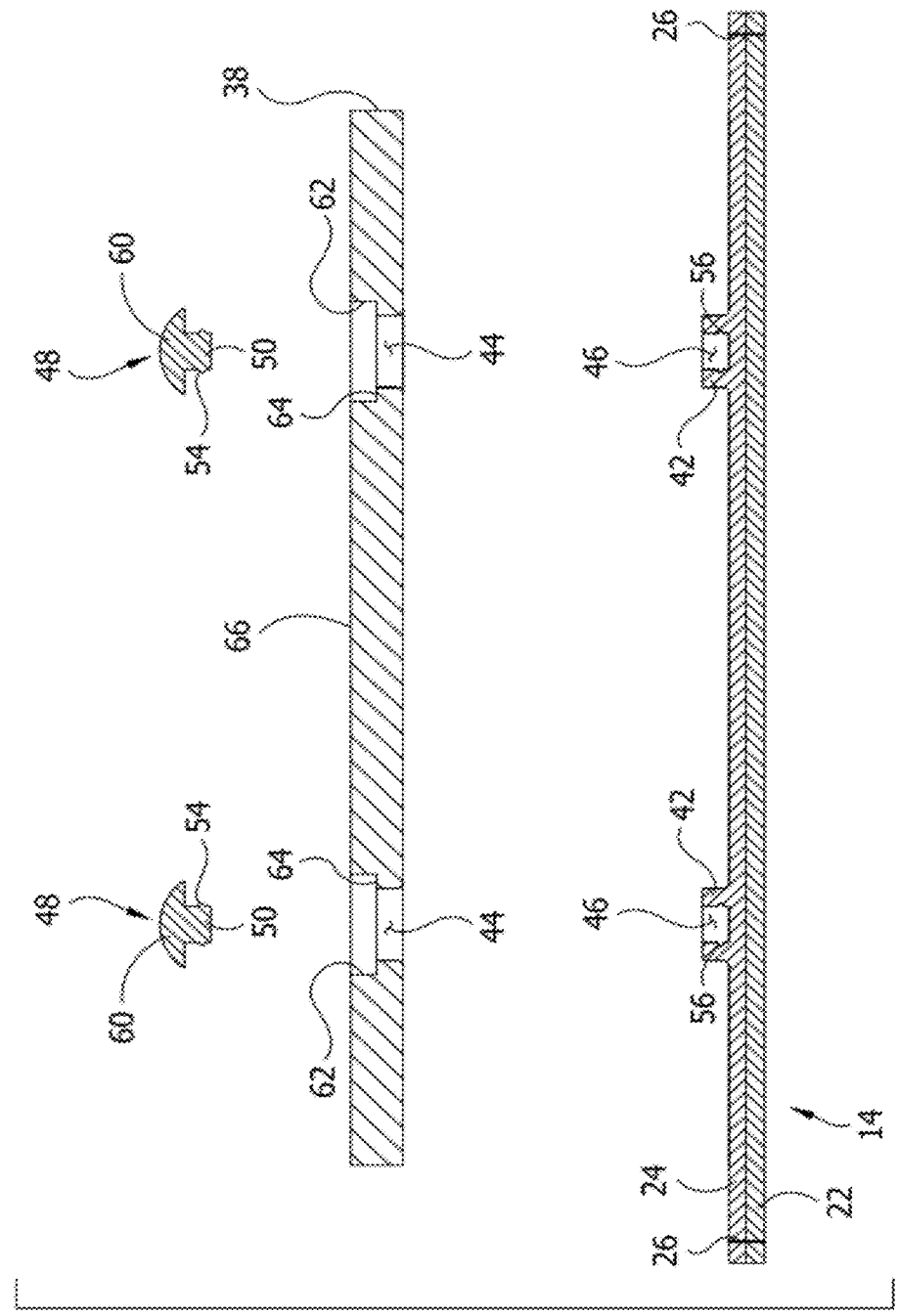

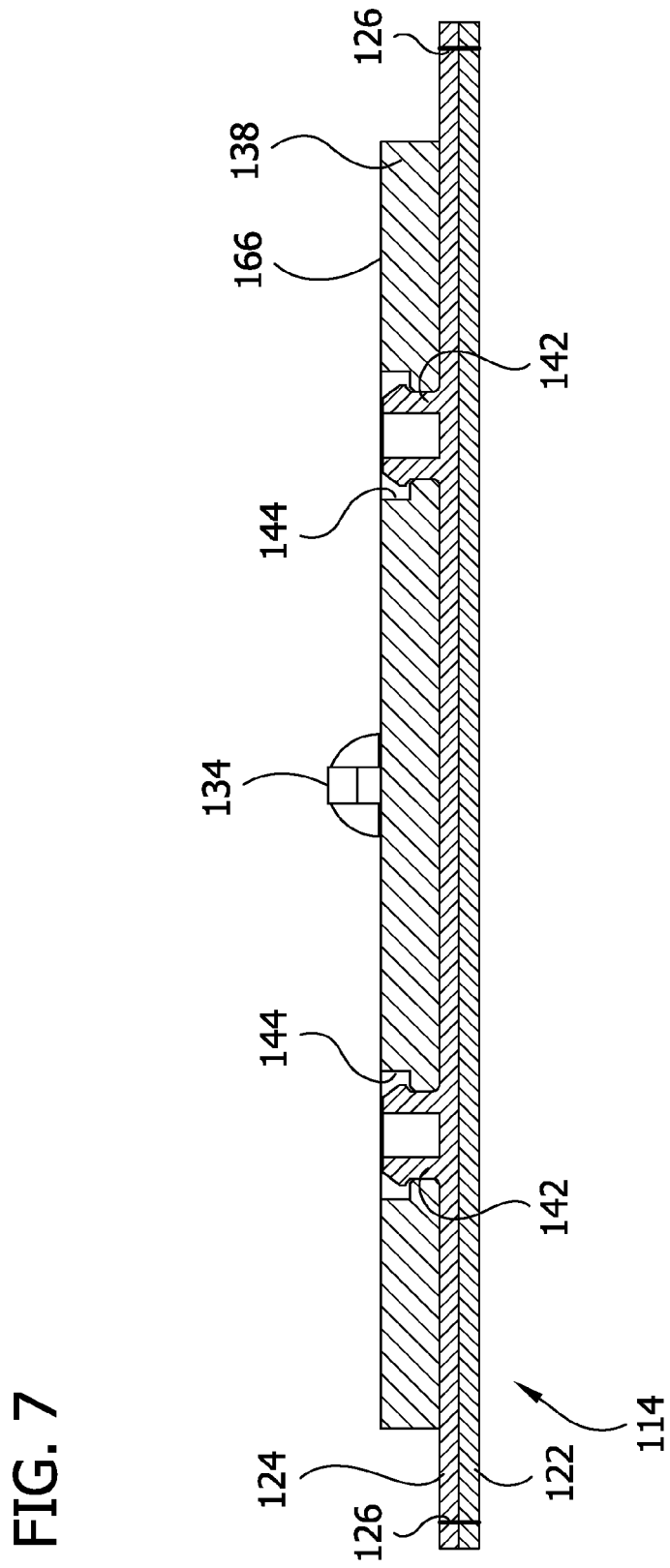

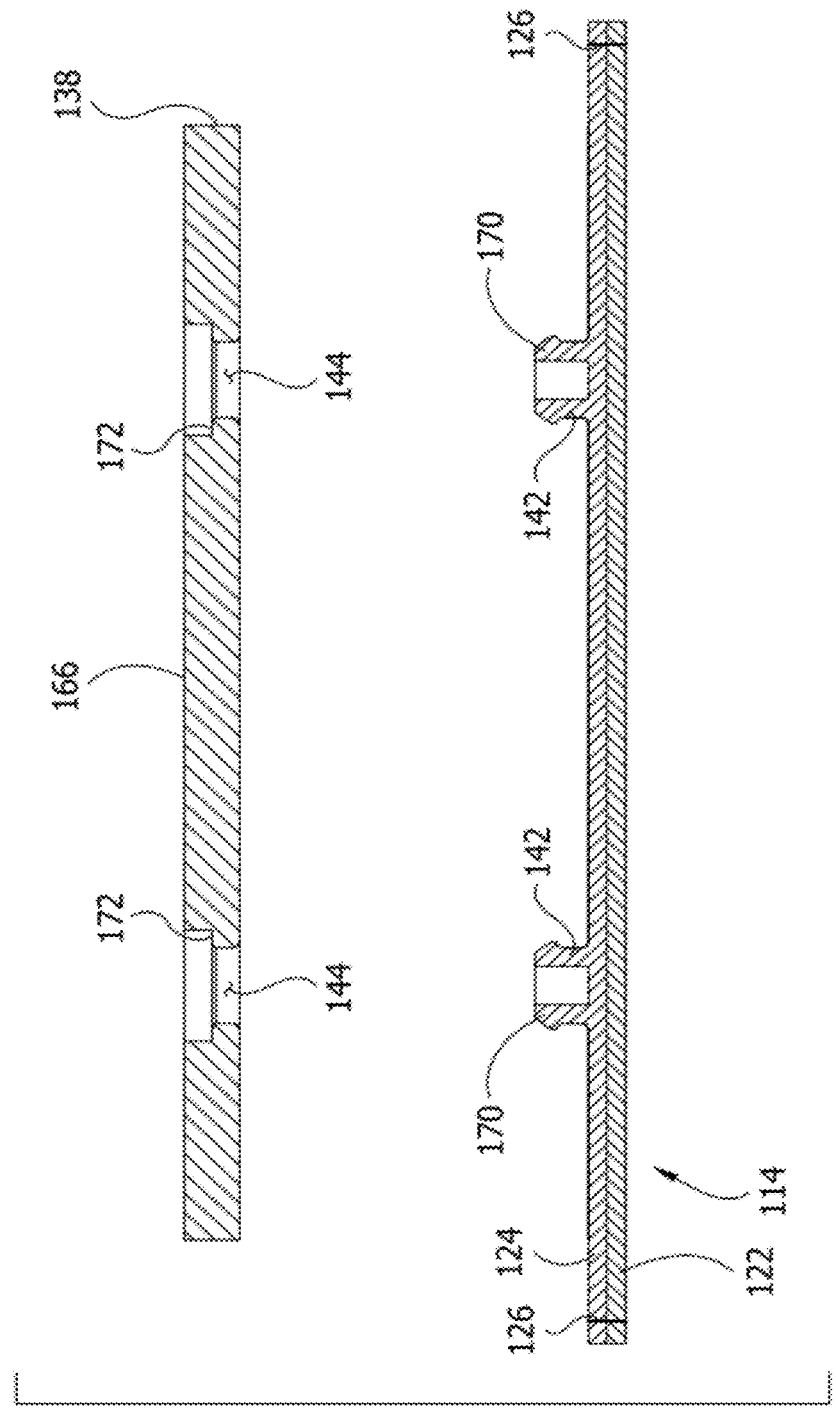

COMPRESSION DEVICE WITH SOLE

BACKGROUND

The present disclosure relates generally to a compression device. In particular, the present disclosure relates to a compression device configured for applying compressive forces to a portion of a wearer's anatomy.

Compression devices for applying compressive forces to a selected area of a wearer's anatomy are generally employed to improve blood flow in the selected area. Compression devices that provide intermittent pulses of a compressed fluid (i.e. air) to inflate at least one inflatable chamber in a cuff or sleeve are particularly useful. This cyclic application of pressure provides a non-invasive method of prophylaxis to reduce the incidence of deep vein thrombosis (DVT), and the like. These compression devices find particular use during surgery on patients with high-risk conditions such as obesity, advanced age, malignancy, or prior thromboembolism. Patients who develop this condition often have swelling (edema) and tissue breakdown (venous stasis ulcer) in the lower leg. When a DVT occurs, the valves that are located within the veins of the leg can be damaged, which in turn can cause stasis and high pressure in the veins of the lower leg.

Generally, these compression devices are fluidly coupled to a source of pressurized fluid by one or more air tubes. Additionally, each compression device includes a flexible shell having one or more bladders disposed therein. The compression device is placed around the patient's foot or other selected portion whereupon a pressurized fluid is delivered into the bladder creating pressure at the part or parts of the body in contact with the bladder.

Compression cuffs adapted for use with a patient's foot may be used by themselves or combined with one or more additional compression cuffs or sleeves that are disposed on portions of a patient's leg for improving the treatment regimen. In general, each of the additional compression sleeves includes a plurality of separate inflatable chambers that are progressively arranged along a longitudinal axis of the sleeve from a lower portion to an upper portion of the limb. A pressure source, e.g. a controller, is provided for intermittently forming a pressure pulse within these inflatable chambers from a source of pressurized fluid during periodic compression cycles. The compression sleeves provide a pressure gradient along the patient's limbs during these compression cycles which progressively decreases from the lower portion to the upper portion of the limb (e.g. from the ankle to the thigh).

Compression cuffs that are adapted for use with a patient's foot generally include a heel strap with a tab portion that is adapted to fit around a portion of the patient's heel. This arrangement allows the compression cuff to be wrapped around and releasably attached to the patient's foot. The compression cuff may include a generally rigid sole to direct expansion of the inflatable chamber toward the wearer's foot. The rigid sole needs to be located under that portion of the inflatable that is acting on the portion of the foot to produce blood flow out of the foot. Conventionally, the rigid sole is temporarily attached to the bladder by double stick tape. Final location and positioning of the rigid sole may be carried out by stitching. For example, the bladder is typically stitched to an outer wrap of the foot cuff. The stitching can be arranged so that it captures the rigid sole in position relative to the bladder, as well as the outer wrap. This requires care and precision in manufacturing the foot cuff.

Examples of compression cuffs are disclosed in U.S. Pat. Nos. 4,013,069 and 4,030,488 to Hasty, U.S. Pat. Nos. 4,029,087 and 5,795,312 to Dye, U.S. Pat. No. 5,626,556 to Tobler et al., and U.S. patent application Ser. No. 11/761,212 to Meyer et al., all of which are currently owned by Tyco Healthcare Group LP and are incorporated by reference herein in their entireties. Other examples of compression cuffs are disclosed in U.S. Pat. No. 4,696,289 to Gardner et al., U.S. Pat. No. 5,989,204 to Lina and U.S. Pat. No. 5,345,260 to Cook. An example of compression treatment method is disclosed in U.S. Pat. No. 6,231,532 to Watson et al., which is owned by Tyco Healthcare Group LP, the contents of which are hereby incorporated by reference herein in their entirety.

SUMMARY

In one aspect, a compression device for applying compression to a part of a wearer's body generally comprises an inflatable member including first and second of fluid impermeable layers secured to one another to define an inflatable chamber. The device comprises a generally rigid counterforce component and connection structure interconnecting the inflatable member and the counterforce component. The connection structure includes a connecting receptacle associated with one of the inflatable member and the counterforce component. A projecting connector extends from the other of the inflatable member and the counterforce component. The projecting connector is received in the connecting receptacle for interconnecting the inflatable member and the counterforce component.

In another aspect, a foot cuff device for applying compression to a foot of a wearer generally comprises an inflatable member including first and second of fluid impermeable layers secured to one another to define an inflatable chamber. A generally rigid sole has an opening. A connection structure interconnects the inflatable member and the counterforce component. The connection structure includes a connecting receptacle associated with one of the inflatable member and the counterforce component. A projecting connector extending from the other of the inflatable member and the counterforce component is received in the connecting receptacle for interconnecting the inflatable member and the counterforce component.

In yet another aspect, a method of making a foot cuff device for applying compression to a foot of a wearer generally comprises forming a bladder by joining together generally opposed layers of fluid impermeable material, and forming a first element of a connection structure on at least one of the layers. A generally rigid counterforce component is formed to have a second element of a connection structure. One of the first and second elements comprises a connecting receptacle and the other of the first and second connector elements comprises a projecting connector. The projecting connector is caused to be received in the connecting receptacle for use in connecting the counterforce component to the bladder.

Other features will be in part apparent and in part pointed out hereinafter. Various refinements exist of the features noted in relation to the above-mentioned aspects of the present invention. Further features may also be incorporated in the above-mentioned aspects of the present invention as well. These refinements and additional features may exist individually or in any combination. For instance, various features discussed below in relation to any of the illustrated embodiments of the present invention may be incorporated into any of the above-described aspects.

BRIEF DESCRIPTION OF THE DRAWINGS

FIG. 4A is an exploded view of FIG. 4;

FIG. 7 is a section of the bladder with attached sole taken along the line 7-7 in FIG. 5;

FIG. 7A is an exploded view of FIG. 7;

Corresponding reference characters indicate corresponding parts throughout the drawings.

DETAILED DESCRIPTION

Figure 1:
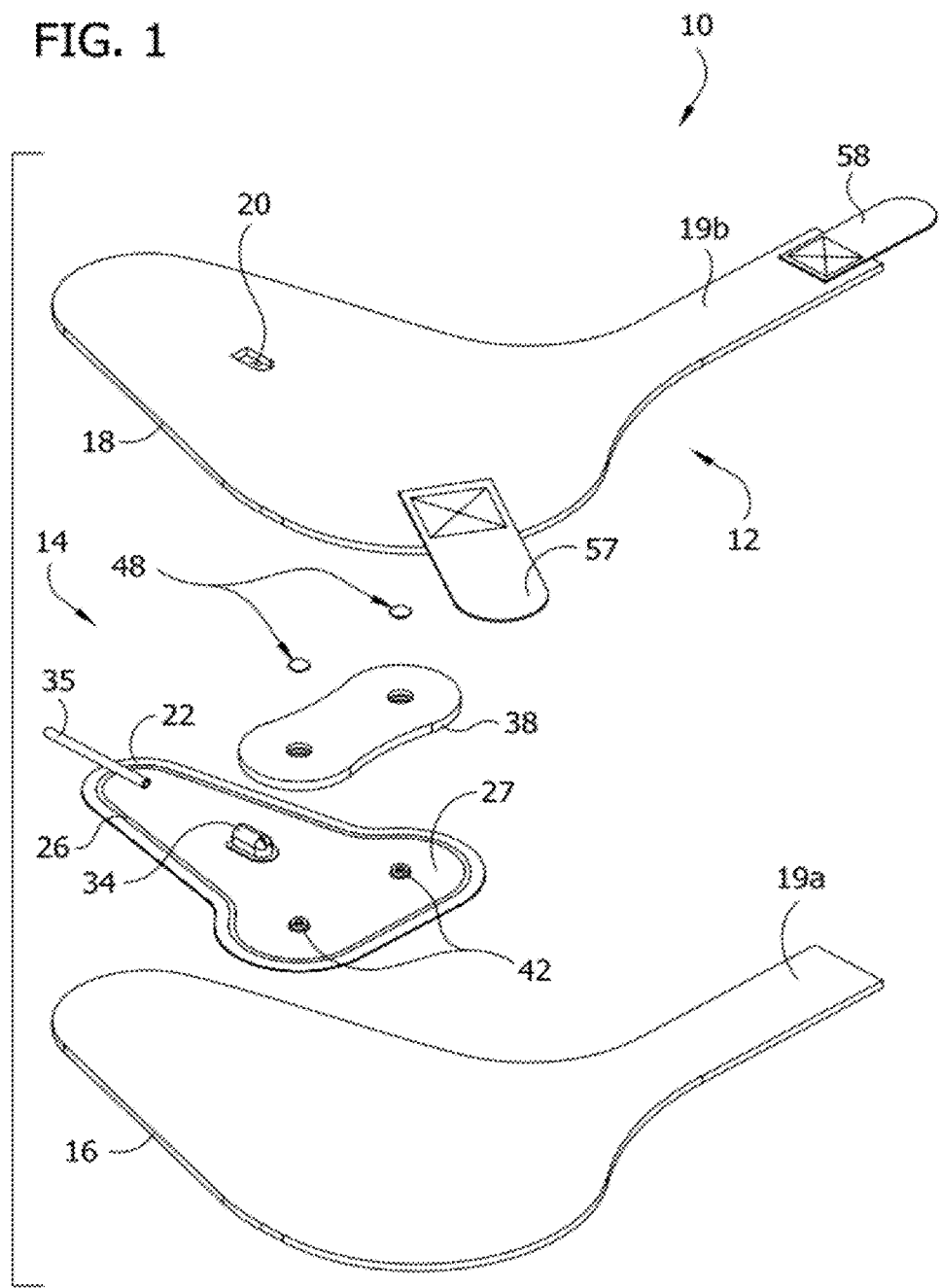
FIG. 1 is an exploded perspective of a first embodiment of a compression foot cuff in accordance with the present disclosure.
Figure 2:
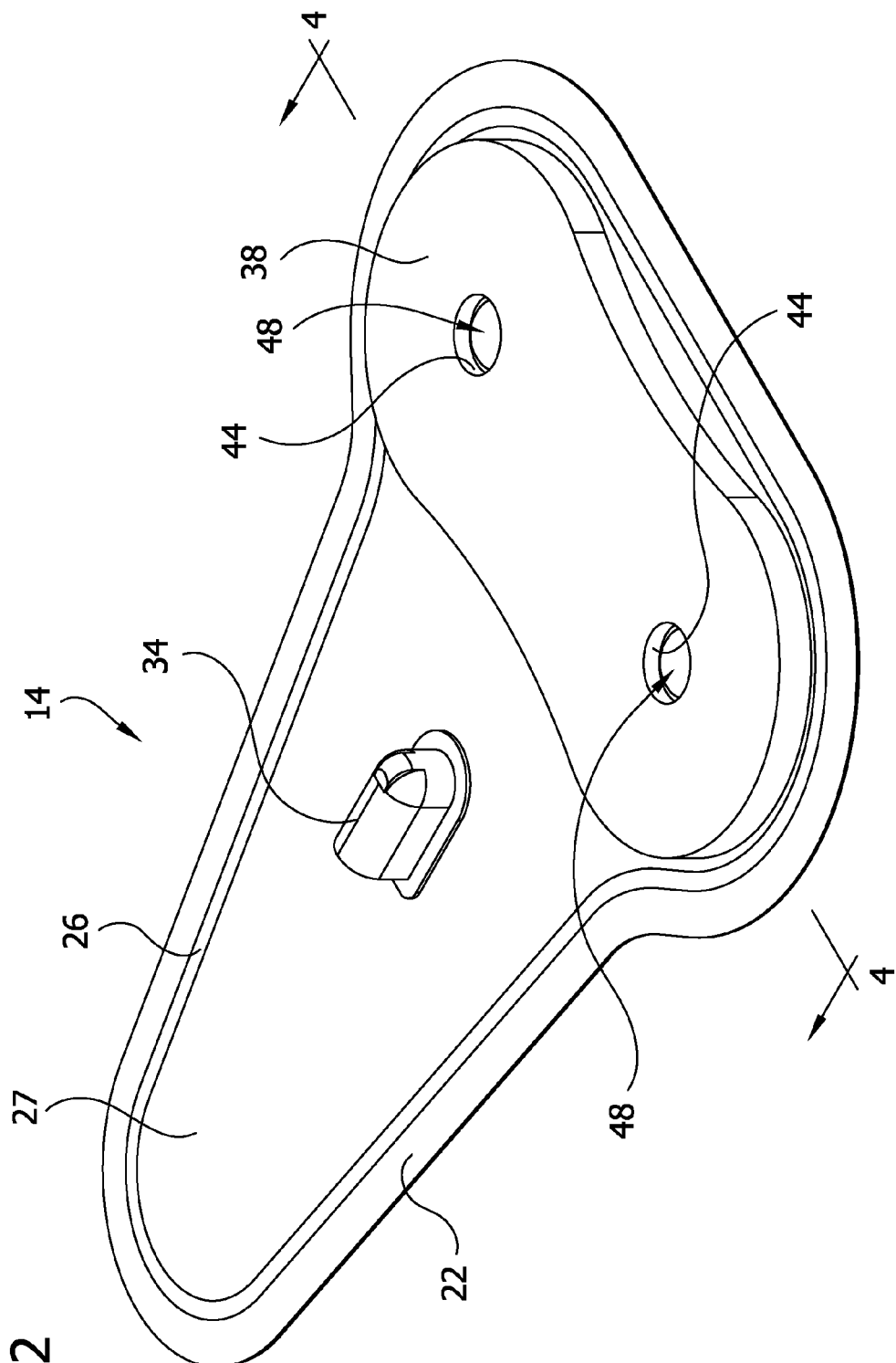
FIG. 2 is a bottom perspective of a bladder of the foot cuff with a sole attached thereto.

With reference to the drawing figures, in which like references numerals identify identical or corresponding elements, various embodiments of the presently disclosed compression apparatus will now be described in detail.

With initial reference to FIGS. 1-4 and 4A, a first embodiment of a compression device in accordance with the present disclosure is illustrated and is designated generally as foot cuff 10. The foot cuff is adapted for use in a compression therapy system for applying compressive pressure to a foot of a wearer. The illustrated foot cuff 10 is configured and dimensioned for disposing about the right foot of the subject. It is understood that the foot cuff 10 may take on other configurations within the scope of the present invention. It is also understood that other types of compression devices besides foot cuffs, including but not limited to leg compression sleeves, arm compression sleeves and other devices are within the scope of the present invention.

As shown best in FIG. 1, the foot cuff 10 includes an envelope, generally indicated at 12, substantially enveloping or enclosing a bladder, generally indicated at 14. The envelope 12 includes an inner contact layer 16 and an outer layer 18 secured to one another generally adjacent to corresponding perimeters of the layers to define an interior space for receiving and substantially enclosing the bladder 14 (broadly, "an inflatable member") therein. The contact layer 16 and the outer layer 18 may be fixedly secured to one another, such as by heat welding, adhesives, sewing or other suitable ways. Alternatively, the contact layer 16 and the outer layer 18 may be releasably secured to one another. In use the contact layer 16 is adjacent to the wearer's foot and the outer layer 18 is located farthest from the foot. As used herein, the terms "inner" and "outer" indicate relative positions of respective components and surfaces with respect to the skin of the wearer's body part when the compression device is secured to the body part, and as such, an "inner" component or surface is more adjacent to the skin of the body part than an "outer" component or surface.

Contact layer 16 and outer layer 18 of the envelope 12 include ankle strap portions 19a and 19b respectively. Ankle strap portions 19a, 19b have a longitudinally projecting configuration for wrapping about a portion of the foot adjacent to the ankle. The ankle strap portions 19a, 19b can be sewn, RF welded, or sonic welded. However, in the illustrated embodiments, the ankle strap portions 19a, 19b are formed as one piece with the contact layer 16 and outer layer 18, respectively.

Contact layer 16 of the envelope 12 is adapted for contacting the foot. Contact layer 16 is in one embodiment fabricated from a chemically treated material, with wicking ability, for wicking away moisture from the skin. In one embodiment, contact layer 16 includes a mesh-like fabric capable of wicking moisture away from the patient's skin. Furthermore, the contact layer 16 can be faced with a soft material toward the treatment surface of the patient. For example, the material can be a thin layer of open celled porous foam, napped cloth, or a layer of vapor permeable cloth permeable. It is understood that the cuff 12 may not include a contact layer within the scope of the present invention.

Outer layer 18 of the envelope 12 includes an opening 20 for permitting a pressurized fluid inlet passage therethrough. Outer layer 18 is configured for providing the attachment surface for a hook and loop feature of cuff 12, as will be described in more detail herein below. Moreover, the outer layer 18 provides a soft material for cushioning effect against the top portion of the feet and may be fabricated from similar materials as contact layer 16 and in similar dimensions therewith for corresponding geometry. Alternatively, outer layer 18 may be fabricated from a laminated material, such as, for example, sontara fabric, open cell urethane foam, or loop fabric. It is understood that the cuff 12 may not include an outer layer within the scope of the present invention.

Figure 4:
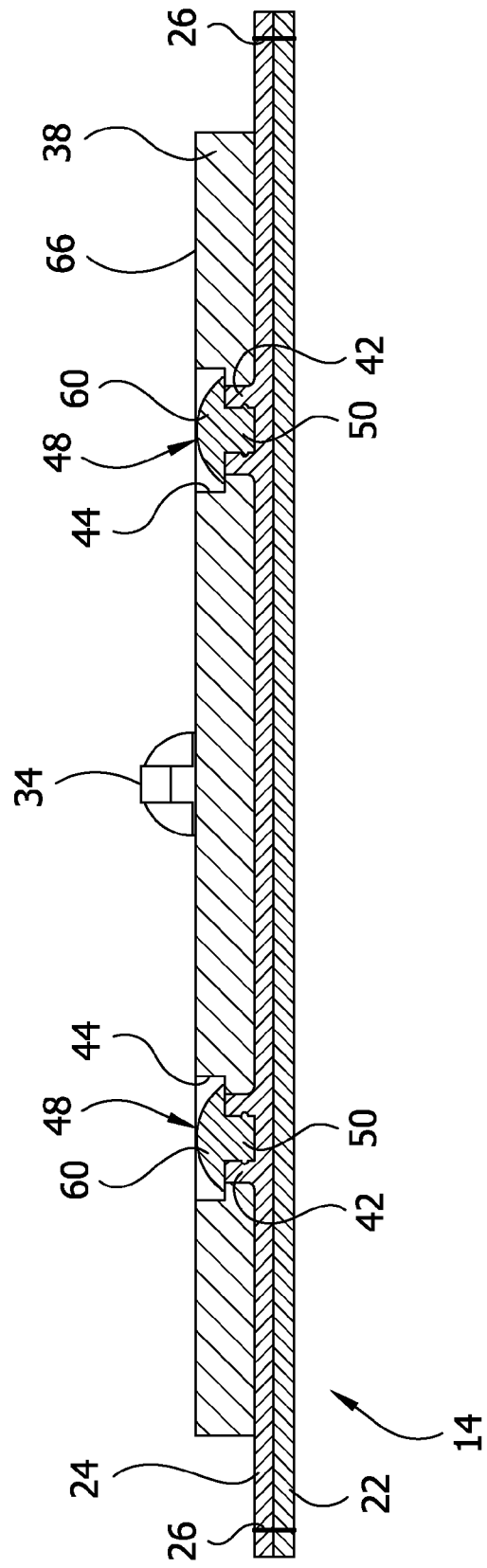
FIG. 4 is a section of the bladder with attached sole taken along the line 4-4 in FIG. 2.
Figure 5:
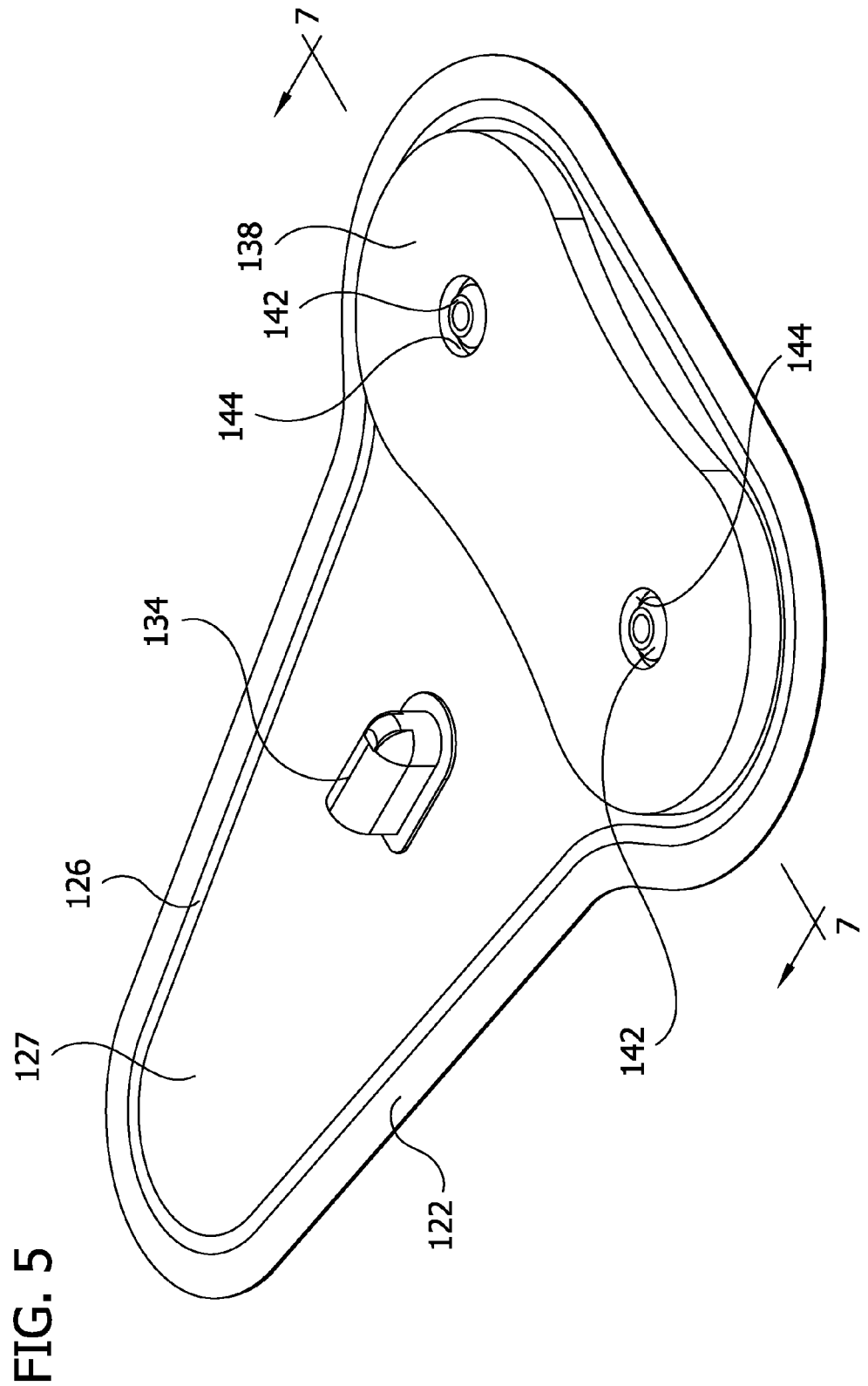
FIG. 5 is a bottom perspective of a second embodiment of a bladder with a sole attached thereto.
Figure 6:
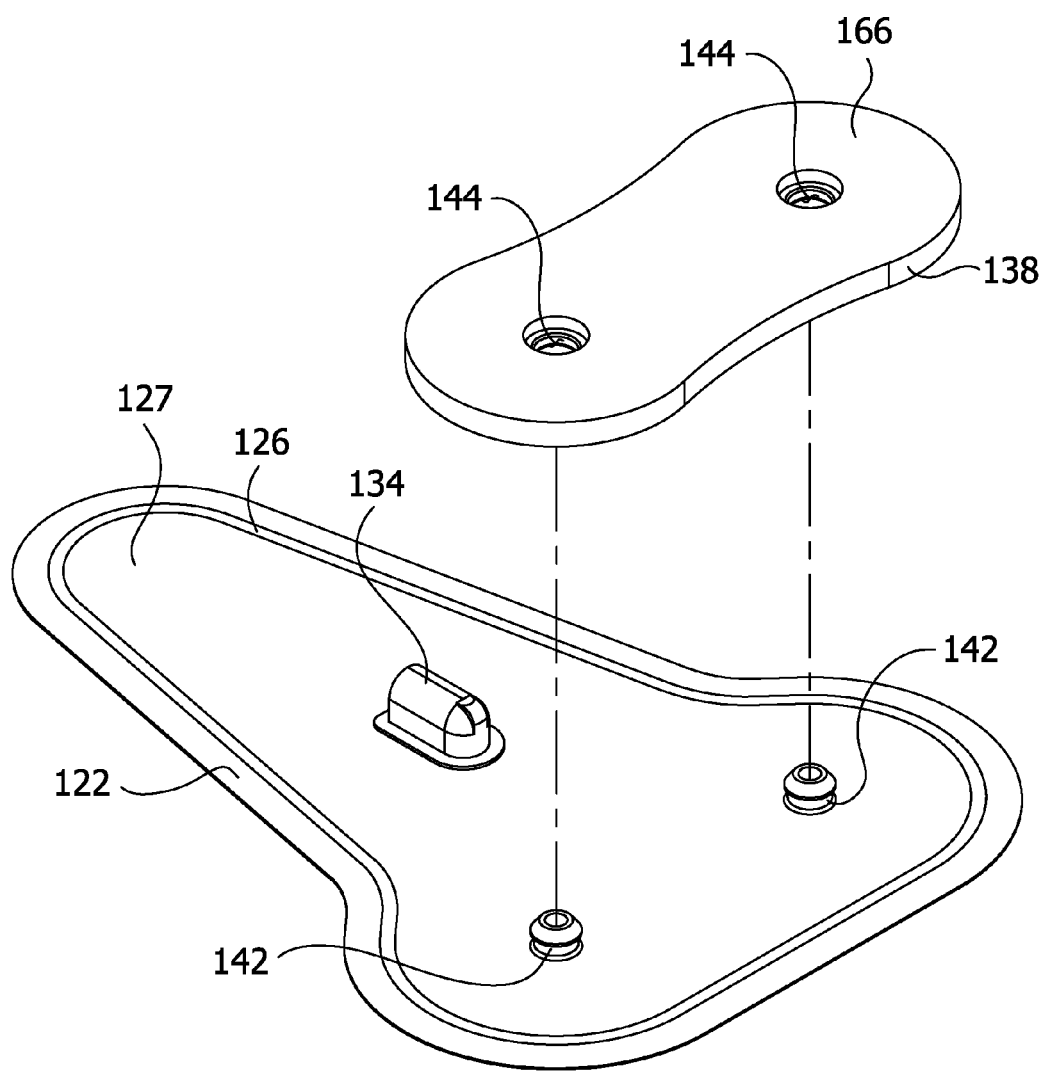
FIG. 6 is an exploded view of FIG. 5.

The bladder 14 is configured for positioning against the bottom portion of the foot. Referring to FIG. 4, bladder 14 includes outer and inner layers 22, 24 of air impermeable material (e.g., PVC) joined together in a suitable manner along a line 26 adjacent to their peripheries to define a single inflatable chamber 27. The layers 22, 24 may be joined to one another in a suitable manner such as by radio frequency (RF) welding. Other ways of joining the layers 22, 24 include sewing, adhesive, heat sealing, etc. It is understood that the bladder 14 can include more than one inflatable chamber 27 within the scope of the present invention. The inflatable chamber 27 of the bladder 14 is adapted for receiving and retaining a pressurized fluid (e.g. air) for exerting compressive pressure to the foot during successive pressure application cycles. The inflatable chamber 27 has an inlet member 34 and a tube 35 connected to the inlet member for air or fluid to be introduced into the chamber during the start of a compression cycle and to be exhausted to end the compression cycle. The inlet member 34 of the illustrated embodiment is a plastic component that is secured such as by heat welding or other means to the bladder 14. It is understood that other ways of introducing air or fluid into the chamber 27 are within the scope of the invention.

Referring to FIGS. 2-4 and 4A, a generally rigid sole (broadly, a counterforce component) is attached to the outer layer 22 of the bladder 14. It is believed the sole 38 provides a counterforce to the outer layer 22 of the bladder 14 as the bladder is expanding to direct expansion toward the contact layer 16 and the user's foot. In this way, the inner layer 24 expands outward more than the outer layer 22 to direct compressive force toward the user's foot. For reasons explained below, the sole 38 has openings 44 (broadly, "connecting receptacles"), and more particularly, two spaced apart openings extending through faces of the sole. It is understood that the sole may have one opening or more than two openings without departing from the scope of the present invention. The sole 38 may be constructed from a polypropylene material or other material within the scope of the invention.

Figure 3:
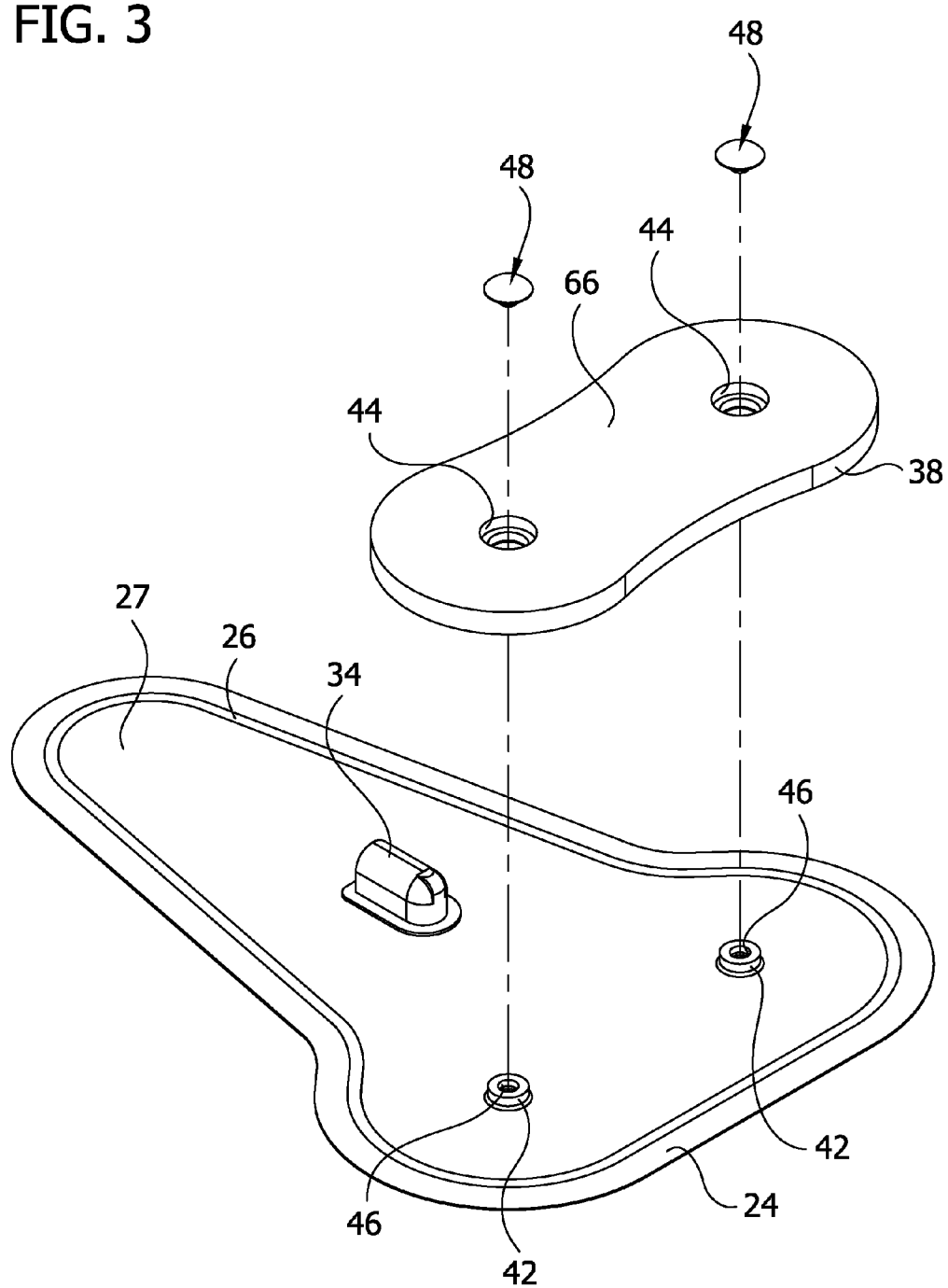
FIG. 3 is an exploded view of FIG. 2.

Referring to FIGS. 3, 4 and 4A, the sole 38 is attached to the outer layer 22 of the bladder 14 using bosses 42 (broadly, "projecting connectors") that extend outward from the outer layer 22 of the bladder 14 and are received in the openings 44 formed in the sole 38. Each boss 42 includes an axial opening or cavity 46 (FIG. 4A) extending through a free end of the boss. Each axial cavity 46 receives a fastener 48 and fixedly retains the fastener therein to attach the sole 38 to the bladder 14. Shafts 50 of the fasteners 48 extend into the respective axial cavities 46 and engage respective interior surfaces 52 of the bosses 42 to retain the fasteners in the bosses. In the illustrated embodiment, the shafts 50 of the fasteners 48 and the interior surfaces 52 of the bosses 42 have respective snap-fit components 54, 56 to retain the fasteners in the bosses. More particularly, the snap-fit components 54 of the fasteners comprise annular projections, and the snap-fit components 56 of the bosses 42 comprise annular grooves for receiving the annular projections of the fasteners. Other types of snap-fit components and other ways of retaining the fasteners 48 in the axial cavities 46 of the bosses 42, including friction fit engagement, threads, and adhesives, is within the scope of the present invention. In this embodiment, the bosses 42, openings 44 and fasteners 48 may be broadly considered "connection structure." The boss 42 may each be considered a projecting connector and the openings 44 may each be considered a connecting receptacle. It is to be understood that the connection structure may have other configurations within the scope of the present invention.

In the illustrated embodiment (FIGS. 4 and 4A), a head 60 of each fastener 48 is received in a counterbore 62 of one of the openings 44 in the sole 38 and contacts an annular surface 64 of the counterbore to press the sole against the outer layer 22 of the bladder 14. The heads 60 of the fasteners 48 and the counterbores 62 are sized and shaped so that the heads of the fasteners do not protrude out of the openings 44 when the sole 38 is attached to the outer layer 22. In this way, an outer surface 66 of the sole 38 remains generally planar (i.e., free from projections extending outward therefrom).

In the illustrated embodiment, the bosses 42 are formed integrally with the outer layer 22 of the bladder 14 so that the outer layer and the bosses 42 are formed as a one-piece construction. For example, the outer layer 22 may be molded to include the bosses 42. Suitable material for making the integrally formed outer layer and bosses includes PVC, polyurethane, nylon, PET, EVA ABS, suitable grades of polyolefin, and other material. In other embodiments, the bosses 42 may be formed separate from the outer layer 22 and secured to the outer layer such as be heat welding (e.g., radiofrequency welding), adhesive, or other ways.

Hook fasteners 57, 58 are provided for securing the wrapped cuff 12 around a foot, and are positioned on the outer layer 18 of the cuff. Hook fastener 56 is mounted to strap portion 19b of outer layer 18 of foot cuff 12 while hook fastener 58 is mounted on a surface of outer layer 18. In use, when ankle strap portions 19a, 19b are wrapped about the back of the foot, hook fastener 57 engages outer layer 18 to facilitate mounting of foot cuff 12 on the foot. An identification tab (not shown) may also be included for providing information such as the model number and manufacturer name. Hook fasteners 57, 58 may have tabs (not shown) without fastening material thereon to provide convenient gripping locations on the hook fasteners to thereby allow the practitioner to easily remove the hooks from the outer face 18b of outer layer 18. The use and operation of the foot cuff 12 for applying compression therapy to the wearer's foot is generally known in the art and will not be described herein.

Referring to FIGS. 5-7 and 7A, in a second embodiment a sole 138 is secured to an outer layer 122 of a bladder 114 using fastener components 142 or bosses (broadly, "projecting connectors") extending outward from the outer layer and secured in respective openings 144 in the sole (broadly, "connecting receptacles"). Corresponding parts of the bladder 114 and the sole 138 of the second embodiment are given the same reference numerals as in the first embodiment, plus 100. In this embodiment, the fastener components 142 extending from the outer layer 122 attach the sole to the bladder 114 without the need for a separate fastener. In the illustrated embodiment, the fastener components 142 and the openings 144 in the sole 138 include respective snap-fit components 170, 172 that engage one another. As shown best in FIG. 7A, the snap-fit components 170 of the fastener components 142 include annular projections, and the snap-fit components 172 of the openings 144 include annular surfaces for contacting the respective annular projections and locking the fasteners components in the openings. Other ways of securing the fastener components 142 in the openings 144 in the sole 138 are within the scope of the invention. The fastener components 142 are formed integrally with the outer layer 122 of the bladder 114, such as by molding. In other embodiments, the fastener components 142 may be formed separate from the outer layer 122 and secured to the outer layer such as be heat welding (e.g., radiofrequency welding), adhesive, or other ways. In this embodiment, the fastener components 142 and openings 144 may be broadly considered "connection structure." The fastener components 142 may each be considered a projecting connector, and the openings 144 may each be considered a connecting receptacle. Other configurations of the connection structure may be used without departing from the scope of the present invention.

In the illustrated embodiment, free ends of the fastener components 142 do not extend through the respective openings 144 (see FIG. 7). In this way, the outer surface 166 of the sole 138 remains generally planar (i.e., free from projections extending outward therefrom). It is understood that the openings 144 in the sole 138 do not have to extend through the sole; the openings may be blind bores or cavities.

Figure 8:
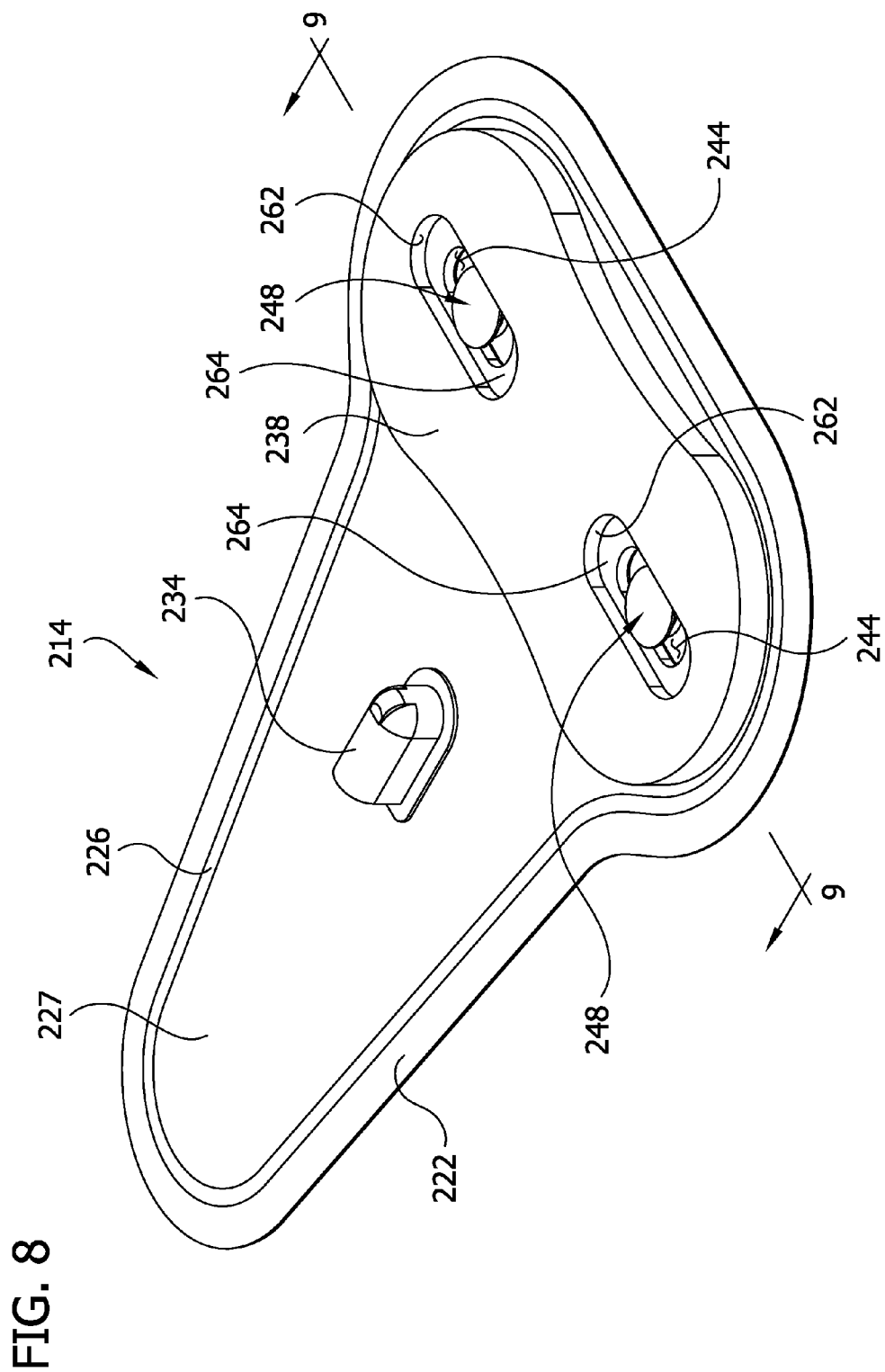
FIG. 8 is a bottom perspective of a third embodiment of a bladder with a sole attached thereto.
Figure 9:
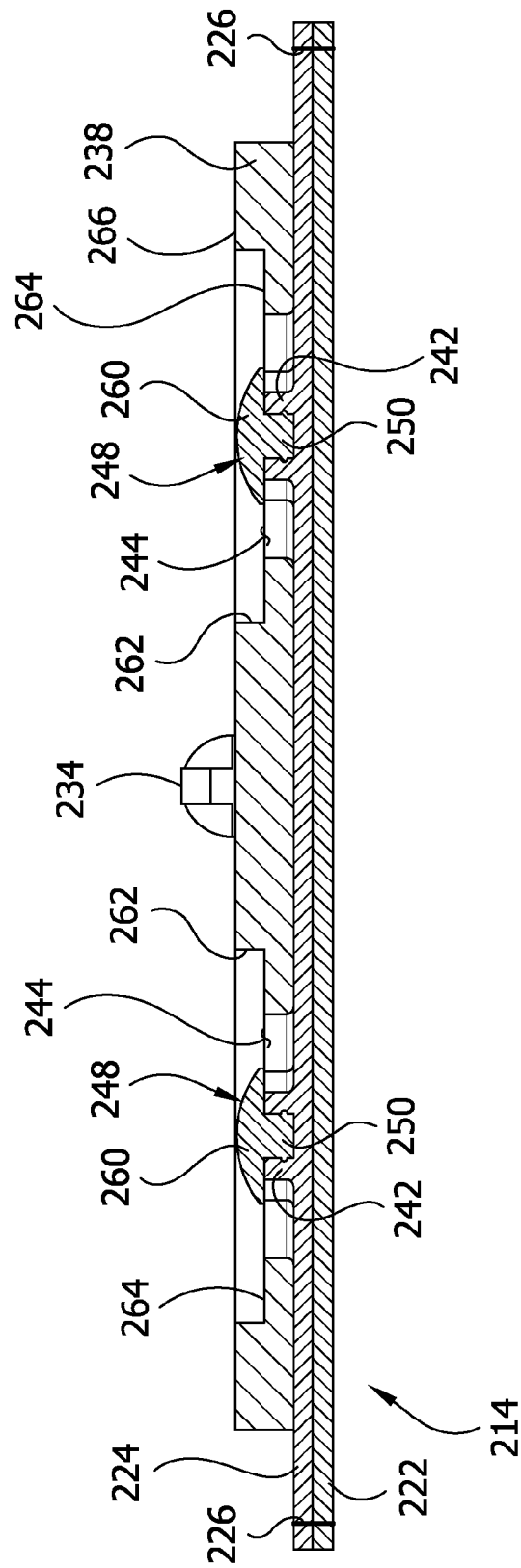
FIG. 9 is a section of the bladder with attached sole taken along the line 9-9 in FIG. 8.

Referring to FIGS. 8 and 9, in a third embodiment a sole 238 is secured to an outer layer 222 of a bladder 214 in a similar manner as the first embodiment illustrated in FIGS. 1-4A, and therefore, like components are indicated by corresponding reference numerals, plus 200. The difference between the sole 238 in the third embodiment and the sole 38 in the first embodiment is that openings 244 in the sole in the third embodiment are generally oblong to permit restricted movement of the sole relative to the bladder 214. More specifically, in the illustrated embodiment each opening 244 has a major axis extending along a major axis of the sole 238, and each opening includes a counterbore 262 defining an oblong, annular contact surface 264. The fasteners 248 secure the sole 238 to the bladder 214 while permitting sliding, axial movement of the sole relative to the bladder. In effect, the openings 244 function as tracks for restrictive, sliding movement of the sole 238 relative to the bladder 214. It is believed that allowing restricted, axial movement of the sole 238 relative to the bladder 214 may facilitate full inflation of the inflatable chamber 227.

It will be understood that numerous modifications and changes in form and detail may be made to the embodiments of the present disclosure. It is contemplated that numerous other configuration of the compression apparatus and geometries and orientation of the bladder may be used, and the material of the cuff and/or bladder may be selected from numerous materials other than those specifically disclosed. Therefore, the above description should not be construed as limiting the disclosed compression apparatus but merely as exemplifications of embodiments thereof. Those skilled in the art will envision numerous modifications within the scope of the present disclosure as defined by the claims appended hereto.

What is claimed is:

1. A compression device for applying compression to a part of a wearer's body comprising
an inflatable member including first and second of fluid impermeable layers secured to one another to define an inflatable chamber and an inlet member fluidly interconnected with the inflatable chamber for introducing air or fluid into the inflatable chamber, a generally rigid,
counterforce component,
connection structure interconnecting the inflatable member and the counterforce component, the connection structure including connecting receptacles associated with the counterforce component, and projecting connectors extending from the inflatable member, the connecting receptacles comprising openings extending through the counterforce component, the projecting connectors being formed integrally with one of the layers of the inflatable member and received in the connecting receptacles for interconnecting the inflatable member and the counterforce component, wherein the inlet member is separate from the projecting connectors.

2. A compression device as set forth in claim 1 wherein each of the projecting connectors comprises a boss extending into a respective one of the openings in the counterforce component.

3. A compression device as set forth in claim 2 wherein each boss has an inwardly extending cavity.

4. A compression device as set forth in claim 3 wherein each boss is formed as one piece with one of the layers of the inflatable member.

5. A compression device as set forth in claim 3 wherein the connection structure further comprises fasteners, each of the fasteners extending through a respective one of the openings in the counterforce member and into the cavity of the boss.

6. A compression device as set forth in 5 wherein each of the fasteners includes a head and each opening in the counterforce component includes a counterbore for receiving the head of the fastener, wherein the head of the fastener engages an annular surface of the counterbore to press the counterforce component against the first layer of the inflatable member.

7. A compression device as set forth in claim 6 wherein the head of each of the fasteners is fully received in the counterbore so that the head does not protrude out of the counterbore.

8. A compression device as set forth in claim 5 wherein each of the fasteners and boss are adapted for snap-fitting interconnection.

9. A compression device as set forth in claim 3 wherein each boss and the counterforce component are adapted for snap-fitting interconnection.

10. A compression device as set forth in claim 1 wherein the connection structure permits sliding, axial movement of the counterforce component relative to the inflatable member.

11. A compression device as set forth in claim 10 wherein the connecting receptacle comprises an oblong opening in the counterforce component.

12. A foot cuff device for applying compression to a foot of a wearer comprising
an inflatable member including first and second of fluid impermeable layers secured to one another to define an inflatable chamber,
a generally rigid sole,
connection structure interconnecting the inflatable member and the sole, the connection structure including a connecting receptacle associated with one of the inflatable member and the sole, and a projecting connector extending from the other of the inflatable member and the sole, the projecting connector being received in the connecting receptacle for interconnecting the inflatable member and the sole, and
an envelope member defining an interior space in which the inflatable member and the sole are enclosed, the envelope member including an inner contact layer and an outer layer secured to one another generally adjacent to corresponding perimeters of the layers to define the interior space.

13. A foot cuff device as set forth in claim 12 further comprising two of the projecting connectors and two openings, the projecting connectors being formed integrally with one of the first and second fluid impermeable layers.

14. A foot cuff device as set forth in claim 12 wherein the connection structure permits sliding, axial movement of the sole relative to the inflatable member.

15. A foot cuff device as set forth in claim 14 wherein the connecting receptacle comprises an oblong opening in the sole.

16. A method of making a foot cuff device for applying compression to a foot of a wearer, the method comprising:
forming a bladder by joining together generally opposed layers of fluid impermeable material and an inlet member fluidly interconnected with the bladder for introducing air or fluid into the bladder; forming projecting connectors of a connection structure on at least one of the layers;
forming a generally rigid counterforce component to have openings extending through the rigid counterforce component; and
causing the projecting connectors to be received in the openings for use in connecting the counterforce component to the bladder, wherein the inlet member is separate from the projecting connectors.

17. A method of making a foot cuff device as set forth in claim 16 further comprising pushing fasteners through the openings in the counterforce component into cavities formed in the projecting connectors.

18. A method of making a foot cuff device as set forth in claim 16 wherein causing the projecting connectors to be received in the openings includes snapping the projecting connectors into connection with the openings.

* * * * *